United States Patent
Asnes

(10) Patent No.: US 8,454,668 B2
(45) Date of Patent: Jun. 4, 2013

(54) ANCHORING ELEMENT

(75) Inventor: Kristian Asnes, Molndal (SE)

(73) Assignee: Cochlear Limited, Macquarie University, NSW (AU)

( * ) Notice: Subject to any disclaimer, the term of this patent is extended or adjusted under 35 U.S.C. 154(b) by 508 days.

(21) Appl. No.: 12/601,799

(22) PCT Filed: May 21, 2008

(86) PCT No.: PCT/SE2008/000338
§ 371 (c)(1),
(2), (4) Date: Nov. 24, 2009

(87) PCT Pub. No.: WO2008/143575
PCT Pub. Date: Nov. 27, 2008

(65) Prior Publication Data
US 2010/0209873 A1    Aug. 19, 2010

(30) Foreign Application Priority Data
May 24, 2007    (SE) ..................... 0701243

(51) Int. Cl.
*A61B 17/04* (2006.01)
*A61B 17/86* (2006.01)
*A61F 2/08* (2006.01)

(52) U.S. Cl.
USPC ........................................... 606/307

(58) Field of Classification Search
USPC .............. 606/300, 305, 307, 321, 329, 319, 606/324; 433/174
See application file for complete search history.

(56) References Cited

U.S. PATENT DOCUMENTS

| | | | |
|---|---|---|---|
| 4,495,917 A | 1/1985 | Byers | |
| 4,498,461 A | 2/1985 | Hakansson | |
| D294,295 S | 2/1988 | Brånemark | |
| 4,936,851 A * | 6/1990 | Fox et al. .................. | 623/16.11 |
| 6,413,259 B1 | 7/2002 | Lyons et al. | |
| 6,685,707 B2 * | 2/2004 | Roman et al. ................ | 606/916 |
| 7,074,222 B2 | 7/2006 | Westerkull | |
| 7,116,794 B2 | 10/2006 | Westerkull | |
| 2003/0055311 A1 | 3/2003 | Neukermans et al. | |
| 2006/0093175 A1 | 5/2006 | Westerkull | |

FOREIGN PATENT DOCUMENTS

| | | |
|---|---|---|
| WO | 2004006792 A1 | 1/2004 |
| WO | 2005/037153 A1 | 4/2005 |
| WO | 2006101837 A2 | 9/2006 |

OTHER PUBLICATIONS

International Search Report. PCT/SE2008/000338. Mailed Sep. 3, 2008.

* cited by examiner

*Primary Examiner* — Andrew Yang
(74) *Attorney, Agent, or Firm* — Kilpatrick, Townsend & Stockton, LLP.

(57) ABSTRACT

Aspects of the present invention are generally directed to an anchoring element comprising a screw shaped central part, a flange which functions as a stop when the anchoring element is installed into the skull bone, and a tubular peripheral part which is connected to the central part via said flange, wherein the peripheral part together with the central part is arranged to cut into the bone tissue when the anchoring element is installed into the bone tissue.

21 Claims, 1 Drawing Sheet

ANCHORING ELEMENT

CROSS-REFERENCE TO RELATED APPLICATIONS

This application is a national stage application under 35 USC §371 (c) of PCT Application No. PCT/SE2008/000338, entitled "ANCHORING ELEMENT," filed on May 21, 2008, which claims priority from Swedish Patent Application No. 0701243-8, filed on May 24, 2007. This application is related to commonly owned and co-pending U.S. Utility patent application entitled "IMPLANT ABUTMENT," filed Nov. 24, 2009, which is a national stage application of PCT Application No. PCT/SE2008/000337, filed May 21, 2008. This application is also related to commonly owned and co-pending U.S. Utility patent application entitled "VIBRATOR FOR BONE CONDUCTING HEARING DEVICES," filed Nov. 24, 2009, which is a national stage application of PCT Application No. PCT/SE2008/000336, filed May 21, 2008. The entire disclosure

BACKGROUND

1. Field of the Invention

The present invention relates to an anchoring element for permanent anchorage of extra oral prostheses, such as bone anchored hearing aid devices or bone anchored ear or orbital prostheses in the skull bone. The invention is specifically intended to be used in connection with hearing aid devices of the bone conduction type, i e hearing aid devices by which the sound is mechanically transmitted via the skull bone directly to the inner ear of a person with impaired hearing. However, the invention is not limited to this specific application, but can be used in connection with other types of hearing aid devices for anchorage in the skull bone and for ear or orbital prostheses which are also anchored in the skull bone and also for finger prostheses or the like, i e in applications where the bone is forming a relatively thin layer.

2. Related Art

For persons who cannot or do not want to benefit from traditional, air conduction hearing aids there are other types of sound transmitting hearing aids on the market, i e bone anchored hearing aids which mechanically transmit the sound information to a persons inner ear via the skull bone by means of a vibrator. The hearing aid device is connected to an anchoring element in the form of an implanted titanium screw installed in the bone behind the external ear and the sound is transmitted via the skull bone to the cochlea (inner ear), i.e. the hearing aid works irrespective of a disease or damage in the middle ear or not. Penetration of the skin makes the vibratory transmission very efficient.

This type of hearing aid device has been a revolution for the rehabilitation of patients with certain types of impaired hearing, but also as anti-stuttering means. It is very convenient for the patient and almost invisible with normal hair styles. It can easily be connected to the implanted titanium fixture by means of a bayonet coupling, a snap in coupling, magnetic coupling or the like. One example of this type of hearing aid device is described in U.S. Pat. No. 4,498,461. Another example is the Baha® bone anchored hearing aid marketed by Cochlear Bone Anchored Solution AB (previously Entific Medical Systems AB) in Goteborg, Sweden. In WO 2005/037153 it is described how this type of hearing aid device can be used as anti stuttering means.

Fixtures used so far for bone anchored hearing aid devices of the type which have been mentioned here as well as for existing ear or orbital prostheses, have been designed in such a way that a screw tap has been required to form an internal thread in the hole drilled in the skull bone or they have been self-tapping. One example of the first mentioned type of fixture is illustrated in US Des. 294,295. This fixture has an external thread with small cutting edges with only a minor scraping effect in the pre-tapped bone hole. It has also a flange which functions as a stop against the bone surface when the fixture is screwed down into the skull bone. The flange is also in this case provided with through holes for bone ingrowth or the like.

Self-tapping fixtures for bone anchored hearing aid devices have been described in for instance U.S. Pat. Nos. 7,074,222 and 7,116,794. These fixtures can normally be installed in the skull bone without the use of any screw taps. This means that the installation can be carried out in a more simple way.

As the skull bone is relatively thin, that part of the anchoring element which is intended to be inserted into the skull bone is normally shorter than 5 mm, and it is important that the anchoring element is provided with a flange which functions as a stop when the fixture is installed into the thin skull bone. The fixtures are normally made of titanium which material has a known ability to be integrated into the surrounding bone tissue, so-called osseointegration.

It is expected that an increased contact surface between the anchoring element and the surrounding bone tissue would be beneficial for a good and stable anchorage. In other implant fields, for instance in the dental implant field, the length of the fixtures can be increased in order to increase the contact surface to the surrounding jaw bone tissue. However, the possibility to increase the length cannot be used for fixtures intended to be installed in the thin skull bone. As already mentioned the fixture lengths are limited to approximately 5 mm in this case. Instead of length, the thickness of the fixture screw could be increased to some extent. The diameter of a fixture used for a bone anchored hearing aid device is typically within the range of 3.5-5 mm, compared to 3-4 mm for a dental implant fixture. To increase the fixture screw diameter even more would not be practical as such a fixture would be too difficult to install.

SUMMARY

In accordance with one aspect of the present invention, an anchoring element for permanent anchorage of extra oral prostheses is provided. The anchoring element comprises: a screw-shaped central part configured to be inserted into the skull bone; a flange which functions as a stop against the bone surface during installation of the anchoring element into the skull bone; and a tubular peripheral part connected to the screw-shaped central part via said flange, wherein the tubular part and the central part are configured to cut into the skull bone during installation of the anchoring element into the skull bone.

BRIEF DESCRIPTION OF THE DRAWINGS

Illustrative embodiments of the present invention will be described herein with reference to the accompanying figures, in which.

DETAILED DESCRIPTION

One advantage of the present invention is to provide an anchoring element adapted for anchorage in a comparatively thin bone, specifically in the comparatively thin skull bone, and which anchoring element has an increased contact surface to the surrounding bone tissue. In such a way the initial stability of the fixture is improved and a good integration between the anchoring element and the bone can be expected.

According to embodiments of the present invention the anchoring element comprises a screw shaped, central part which is intended to be inserted in the skull bone, a flange which functions as a stop when the fixture is installed into the skull bone and a tubular, peripheral part which is connected to the central part via said flange and which peripheral part together with the central part is arranged to cut into the bone tissue when the anchoring element is installed into the bone tissue.

According to certain embodiments the anchoring element comprises a tubular part which includes a saw tooth edge to cut into the bone tissue when the anchoring element is installed. According to a further embodiment, the tubular part comprises a number of holes for bone ingrowth.

Figure 1:
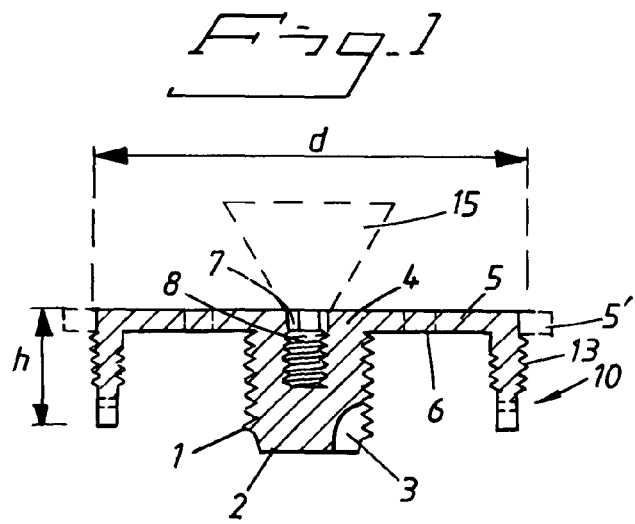
FIG. 1 is a side view of an anchoring element in accordance with embodiments of the invention.

FIG. 1 illustrates an anchoring element in accordance with embodiments of the present invention. In these embodiments, the anchoring element is made of titanium which has a known ability to integrate into surrounding bone tissue, so-called osseointegration. The anchoring element has a central, screw-shaped part 1 which is intended to be installed into the skull bone. The apical portion 2 of the central part 1 is preferably fitted with in this case three self-tapping cutting edges 3. The rear (upper) portion 4 of the central part is integrated with an annular flange 5. The annular flange 5 functions as a stop when the anchoring element is installed into the skull bone when the surface 6 comes into contact with the bone surface. The upper portion of the screw-shaped central part is further provided with a tool engaging socket 7, for instance in the form of an internal hex or the like, for installing the anchoring element. The upper portion is also provided with an internal bore 8 for connecting a skin penetrating part 15, illustrated by means of dotted lines in the figure, for a hearing aid device or an ear or orbital prosthesis. Such parts are known per se and will not be described in any detail here. The screw-shaped part 1 is shorter than 5 mm, so that the screw will not go completely through the thin skull bone when installed, and it has an outer thread diameter of about 3.5-4.0 mm.

Figure 2:
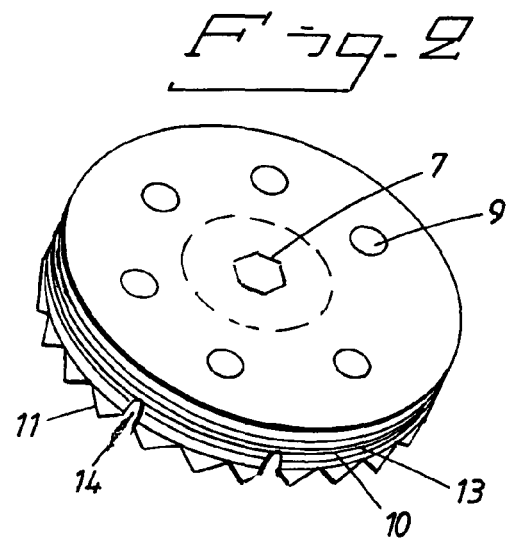
FIG. 2 is an upper view of the anchoring element of FIG. 1.

As illustrated in FIG. 2 the flange has a substantially planar sleeve-shaped design forming together with the upper surface of the central screw shaped part a flat, circular upper surface. This upper flange surface might be closed or it might be provided with a number of through holes 9 for bone ingrowth or for retention when the flange after installation is resting tight against the outer bone surface.

As also illustrated in the figures the peripheral part of the annular flange is integrated with a sleeve-shaped part 10 which is directed downwards, i e towards the bone surface when the anchoring element is installed, and which part is arranged to cut into the bone tissue when the anchoring element is installed. In order to make it easier for the sleeve-shaped part to cut into the bone tissue during installation it might be provided with a saw-tooth edge 11. By means of this sleeve-shaped part the anchoring element provides a circular saw toothed function when it is screwed down into the bone tissue. It should be understood that a more effective bone anchorage is provided with this geometrical design, compared to a conventional fixture geometry, in the skull bone extension. The sleeve-shaped part 10 increases the contact surface against the bone. It also reduces the risk for bacterial ingrowth through the skin as the distance for the bacteria to move to the sensitive bone-implant interface is also increased. The flange 5 might have the same outer diameter as the sleeve-shaped part 10, as illustrated in the figures, but as an alternative it might exceed the outer diameter of the sleeve-shaped part, as indicated by dotted lines 5' in the figure.

As already mentioned the screw-shaped central part might have a maximal extension of 5 mm. The height h of the sleeve-shaped part has also a maximum of 5 mm. This low geometrical design is an advantage compared to conventional fixture designs. The sleeve-shaped part might have a diameter d of about 2 h, ie in this case approximately 10 mm.

Figure 3:
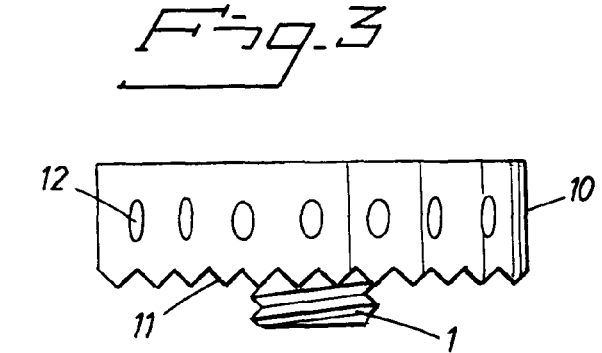
FIG. 3 illustrates several examples of a_tubular part in accordance with embodiments of the present invention.

The sleeve-shaped part 10 might be provided with a number of through holes 12 for bone ingrowth, see FIG. 3. Furthermore, the sleeve-shaped part might be provided with an outer and/or inner thread 13 or rills in order to increase the retention to the surrounding bone tissue. The threaded portion of the sleeve-shaped part might have self tapping cutting edges 14 similar to the fixture-like central part.

The invention is not limited to the embodiments illustrated in the figures but can be varied within the scope of the accompanying claims. Specifically, it should be understood that the part of the anchoring element which is intended to be inserted into the skull bone could be provided with a surface coating, used in the art to promote and stimulate healing of the anchoring element into the bone. Furthermore, the anchoring element could be provided with an external tool-engaging portion instead of the internal one illustrated in the figure. Instead of connecting a separate skin penetrating part such a part might be integrated with the anchoring element itself so that a one piece implant is formed.

It will be appreciated by persons skilled in the art that numerous variations and/or modifications may be made to the invention as shown in the specific embodiments without departing from the spirit or scope of the invention as broadly described. For example, it should be understood that the anchoring element is intended to be used for bone-anchored hearing aid devices for persons with hearing problems but also for persons with stuttering problems. Even if the invention has been described in connection with bone-anchored hearing aid devices it should be understood that it could be used for other types of extra oral prostheses such as finger prostheses or the like. The present embodiments are, therefore, to be considered in all respects as illustrative and not restrictive.

Further features and advantages of the present invention may be found in commonly owned and co-pending U.S. Utility patent application entitled "IMPLANT ABUTMENT," filed Nov. 24, 2009, which is a national stage application of PCT Application No. PCT/SE2008/000337, filed May 21, 2008; and in commonly owned and co-pending U.S. Utility patent application entitled "VIBRATOR FOR BONE CONDUCTING HEARING DEVICES," filed Nov. 24, 2009, which is a national stage application of PCT Application No. PCT/SE2008/000336, filed May 21, 2008. The entire disclosure and contents of these applications are hereby incorporated by reference herein.

The invention claimed is:

1. An anchoring element for permanent anchorage of extra oral prostheses, comprising:
    a screw-shaped central part configured to be inserted into the skull bone;
    a flange which functions as a stop against the bone surface during installation of the anchoring element into the skull bone; and
    a tubular peripheral part connected to the screw-shaped central part via said flange, wherein the tubular part and the central part are configured to cut into the skull bone during installation of the anchoring element into the skull bone, wherein the flange fixedly connects the tubular peripheral part to the screw-shaped central part such that the tubular peripheral part is non-rotatably fixed relative to the screw-shaped central part.

2. The anchoring element according to claim 1, wherein the tubular part has a saw-toothed edge to cut into the bone during installation of the anchoring element.

3. The anchoring element according to claim 1, wherein the tubular part has one or more of external and internal threads or rills.

4. The anchoring element according to claim 3, wherein the threads each comprise one or more self-tapping cutting edges.

5. The anchoring element according to claim 1, wherein the tubular part comprises a number of holes for bone ingrowth.

6. The anchoring element according to claim 1, wherein the flange and central part form a substantially planar upper surface.

7. The anchoring element according to claim 1, wherein an overall thickness of the anchoring element is less than approximately 5 mm.

8. The anchoring element according to claim 1, wherein the central part comprises
a central opening extending down into the screw-shaped central part.

9. The anchoring element according to claim 8, wherein the central opening is configured to receive a tool.

10. The anchoring element according to claim 8, wherein the central opening is configured for connection with a skin penetration element for an external part of the prosthesis.

11. The anchoring element according to claim 1, wherein the element is configured to anchor a bone anchored hearing aid device to the skull bone.

12. The anchoring element according to claim 1, wherein the element is configured to anchor an orbital prostheses to the skull bone.

13. An anchoring element for permanent anchorage of an extra oral prostheses, comprising:
a screw-shaped central part configured to be inserted into the skull bone, the central part including an outer facing bone cutting and engaging surface;
a flange which functions as a stop against the bone surface during installation of the anchoring element into the skull bone, the flange extending outwardly from the screw-shaped central part; and
a tubular peripheral part connected to the central part via said flange, the peripheral part including an inner surface that is spaced away from the outer surface of the central part, defining a recess therebetween, the peripheral part including at least one of an outer facing or an inner facing bone cutting and engaging surface, wherein the peripheral part and the central part are configured to simultaneously cut into the skull bone during rotation of the anchoring element relative to the skull bone.

14. The anchoring element of claim 13, wherein the tubular peripheral part includes both the outer facing and inner facing bone cutting and engaging surfaces.

15. The anchoring element of claim 14, wherein the tubular peripheral part further comprises a downward facing bone cutting surface.

16. The anchoring element of claim 13, wherein an overall thickness of the anchoring element is less than approximately 5 mm and wherein an overall diameter of the anchoring element is greater than the overall thickness.

17. An anchoring element for permanent anchorage of an extra oral prosthesis, comprising:
at least two separate cutting surfaces configured to simultaneously cut into a skull bone during installation of the anchoring element into the skull bone; and
a stop configured to prevent installation of the anchoring element beyond a predetermined depth;
wherein the at least two separate cutting surfaces are concentric and comprise an outer cutting surface and an inner cutting surface which extends below the outer cutting surface.

18. The anchoring element of claim 17, wherein the stop extends between the two separate cutting surfaces.

19. The anchoring element of claim 18, wherein the two separate cutting surfaces are part of cylindrical surfaces extending downwardly from the stop.

20. The anchoring element of claim 17, wherein an overall diameter of the anchoring element is greater than the overall thickness.

21. The anchoring element of claim 17, wherein the outer cutting surface comprises an outer outward facing cutting surface, an outer inward facing cutting surface, and an outer, downward facing cutting surface, all of which are concentric with the inner cutting surface.

* * * * *